(12) United States Patent
Solem et al.

(10) Patent No.: US 7,192,443 B2
(45) Date of Patent: Mar. 20, 2007

(54) DELAYED MEMORY DEVICE

(75) Inventors: Jan Otto Solem, Stetten (CH); Per Ola Kimblad, Lund (SE)

(73) Assignee: Edwards Lifesciences AG, Saint-Prex (CH)

( * ) Notice: Subject to any disclaimer, the term of this patent is extended or adjusted under 35 U.S.C. 154(b) by 499 days.

(21) Appl. No.: 10/141,348

(22) Filed: May 9, 2002

(65) Prior Publication Data
US 2003/0135267 A1    Jul. 17, 2003

(30) Foreign Application Priority Data
Jan. 11, 2002   (SE)  .................................... 0200073

(51) Int. Cl.
*A61F 2/24*    (2006.01)
(52) U.S. Cl. .................... 623/2.37; 623/1.12; 623/1.16
(58) Field of Classification Search ............... 623/1.12, 623/1.16, 2.36, 2.37
See application file for complete search history.

(56) References Cited

U.S. PATENT DOCUMENTS

| | | | |
|---|---|---|---|
| 4,164,046 A | 8/1979 | Cooley | |
| 4,655,771 A | 4/1987 | Wallsten | |
| 4,954,126 A | 9/1990 | Wallsten | |
| 5,006,106 A | 4/1991 | Angelchik | |
| 5,061,275 A | 10/1991 | Wallsten et al. | |
| 5,064,435 A | 11/1991 | Porter | |
| 5,071,407 A | 12/1991 | Termin et al. | |
| 5,104,404 A | 4/1992 | Wolff | |
| 5,163,955 A | 11/1992 | Love et al. | |
| 5,170,802 A | 12/1992 | Mehra | |
| 5,209,730 A | 5/1993 | Sullivan | |
| 5,224,491 A | 7/1993 | Mehra | |
| 5,304,131 A | 4/1994 | Paskar | |
| 5,382,259 A | 1/1995 | Phelps et al. | |
| 5,383,892 A | 1/1995 | Cardon et al. | |

(Continued)

FOREIGN PATENT DOCUMENTS

DE    196 05 042 A1    1/1998

(Continued)

OTHER PUBLICATIONS

Laaksovirta et al., *Expansion and bioabsorption of the self-reinforced lactic and glycolic acid copolymer prostatic spiral stent*, PubMed, Excerpt from J Urol Sep. 2001; 166(3):919-22, one sheet.

(Continued)

*Primary Examiner*—Julian W. Woo
*Assistant Examiner*—Sarah Webb
(74) *Attorney, Agent, or Firm*—David L. Hauser

(57) ABSTRACT

A medical device and a method for providing a change of shape in a part of the body of an organism. The device is insertable into the body of the organism and comprises a member having a preferred state of shape and having a tendency to transfer its shape towards said preferred state of shape when being in a non-preferred state of shape. The device further comprises a resorbable means which is arranged to hold the member in the non-preferred state of shape and to delay the transfer when the device is inserted into the body of the organism by counteracting said transfer during resorption of the resorbable means by the surrounding body of the organism.

18 Claims, 11 Drawing Sheets

U.S. PATENT DOCUMENTS

| | | |
|---|---|---|
| 5,390,661 A | 2/1995 | Griffith et al. |
| 5,441,515 A | 8/1995 | Khosravi et al. |
| 5,449,373 A | 9/1995 | Pinchasik et al. |
| 5,476,471 A | 12/1995 | Shifrin et al. |
| 5,496,275 A | 3/1996 | Sirhan et al. |
| 5,531,779 A | 7/1996 | Dahl et al. |
| 5,534,007 A | 7/1996 | St. Germain et al. |
| 5,545,209 A | 8/1996 | Roberts et al. |
| 5,571,135 A | 11/1996 | Fraser et al. |
| 5,584,879 A | 12/1996 | Reimold et al. |
| 5,591,197 A | 1/1997 | Orth et al. |
| 5,593,442 A | 1/1997 | Klein |
| 5,607,444 A | 3/1997 | Lam |
| 5,674,280 A | 10/1997 | Davidson et al. |
| 5,713,949 A | 2/1998 | Jayaraman |
| 5,741,274 A | 4/1998 | Lenker et al. |
| 5,817,126 A | 10/1998 | Imran |
| 5,824,071 A | 10/1998 | Nelson et al. |
| 5,876,419 A | 3/1999 | Carpenter et al. |
| 5,876,433 A | 3/1999 | Lunn |
| 5,891,108 A | 4/1999 | Leone et al. |
| 5,911,732 A | 6/1999 | Hojeibane |
| 5,919,233 A | 7/1999 | Knopf et al. |
| 5,935,081 A | 8/1999 | Kadhiresan |
| 5,954,761 A | 9/1999 | Machek et al. |
| 5,961,545 A | 10/1999 | Lentz et al. |
| 5,980,552 A | 11/1999 | Pinchasik et al. |
| 6,006,122 A | 12/1999 | Smits |
| 6,013,854 A | 1/2000 | Moriuchi |
| 6,019,739 A | 2/2000 | Rhee et al. |
| 6,027,525 A | 2/2000 | Suh et al. |
| 6,051,020 A | 4/2000 | Goicoechea et al. |
| 6,071,292 A | 6/2000 | Makower et al. |
| 6,077,296 A | 6/2000 | Shokoohi et al. |
| 6,093,203 A | 7/2000 | Uflacker |
| 6,110,100 A | 8/2000 | Talpade |
| 6,123,699 A | 9/2000 | Webster, Jr. |
| 6,161,029 A | 12/2000 | Spreigl et al. |
| 6,161,543 A | 12/2000 | Cox et al. |
| 6,165,169 A | 12/2000 | Panescu et al. |
| 6,171,329 B1 | 1/2001 | Shaw et al. |
| 6,183,411 B1 | 2/2001 | Mortier et al. |
| 6,203,556 B1 | 3/2001 | Evans et al. |
| 6,210,432 B1 | 4/2001 | Solem et al. |
| 6,221,103 B1 | 4/2001 | Melvin |
| 6,248,119 B1 | 6/2001 | Solem |
| 6,250,308 B1 | 6/2001 | Cox |
| 6,264,602 B1 | 7/2001 | Mortier et al. |
| 6,264,691 B1 | 7/2001 | Gabbay |
| 6,325,826 B1 | 12/2001 | Vardi et al. |
| 6,343,605 B1 | 2/2002 | Lafontaine |
| 6,350,277 B1 | 2/2002 | Kocur |
| 6,368,348 B1 | 4/2002 | Gabbay |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,409,760 B1 | 6/2002 | Melvin |
| 6,537,314 B2 | 3/2003 | Langberg et al. |
| 6,569,198 B1 | 5/2003 | Wilson et al. |
| 6,626,899 B2 | 9/2003 | Houser et al. |
| 6,629,534 B1 | 10/2003 | St. Goar et al. |
| 6,656,221 B2 | 12/2003 | Taylor et al. |
| 6,669,687 B1 | 12/2003 | Saadat |
| 6,676,702 B2 | 1/2004 | Mathis |
| 6,706,065 B2 | 3/2004 | Langberg et al. |
| 6,709,456 B2 | 3/2004 | Langberg et al. |
| 6,764,510 B2 | 7/2004 | Vidlund et al. |
| 6,790,231 B2 | 9/2004 | Liddicoat et al. |
| 6,797,001 B2 | 9/2004 | Mathis et al. |
| 6,800,090 B2 | 10/2004 | Alferness et al. |
| 6,810,882 B2 | 11/2004 | Langberg et al. |
| 6,824,562 B2 | 11/2004 | Mathis et al. |
| 6,890,353 B2 | 5/2005 | Cohn et al. |
| 6,908,478 B2 | 6/2005 | Alferness et al. |
| 6,989,028 B2 | 1/2006 | Lashinski et al. |
| 6,997,951 B2 | 2/2006 | Solem et al. |
| 7,011,682 B2 | 3/2006 | Lashinski et al. |
| 7,090,695 B2 | 8/2006 | Solem et al. |
| 2001/0018611 A1 | 8/2001 | Solem et al. |
| 2001/0044568 A1 | 11/2001 | Langberg et al. |
| 2002/0016628 A1 | 2/2002 | Langberg et al. |
| 2002/0019660 A1 | 2/2002 | Gianotti et al. |
| 2002/0022880 A1 | 2/2002 | Melvin |
| 2002/0087173 A1 | 7/2002 | Alferness et al. |
| 2002/0103533 A1 | 8/2002 | Langberg et al. |
| 2002/0111533 A1 | 8/2002 | Melvin |
| 2002/0111647 A1 | 8/2002 | Khairkhahan et al. |
| 2002/0124857 A1 | 9/2002 | Schroeppel |
| 2002/0151961 A1 | 10/2002 | Lashinski et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1* | 12/2002 | Santamore et al. ........ 623/2.36 |
| 2003/0078465 A1 | 4/2003 | Pai et al. |
| 2003/0078654 A1 | 4/2003 | Taylor et al. |
| 2003/0083538 A1 | 5/2003 | Adams et al. |
| 2003/0105520 A1 | 6/2003 | Alferness et al. |
| 2003/0120341 A1 | 6/2003 | Shennib et al. |
| 2003/0130730 A1 | 7/2003 | Cohn et al. |
| 2003/0135267 A1 | 7/2003 | Solem et al. |
| 2003/0144697 A1 | 7/2003 | Mathis et al. |
| 2003/0171806 A1 | 9/2003 | Mathis et al. |
| 2003/0204138 A1 | 10/2003 | Choi |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0102840 A1 | 5/2004 | Solem et al. |
| 2004/0102841 A1 | 5/2004 | Langberg et al. |
| 2004/0133192 A1 | 7/2004 | Houser et al. |
| 2004/0153146 A1 | 8/2004 | Lashinski et al. |
| 2004/0176840 A1 | 9/2004 | Langberg et al. |
| 2004/0267358 A1 | 12/2004 | Reitan |
| 2005/0043792 A1 | 2/2005 | Solem et al. |
| 2005/0060030 A1 | 3/2005 | Lashinski et al. |
| 2005/0080483 A1* | 4/2005 | Solem et al. ............... 623/2.11 |
| 2005/0096740 A1 | 5/2005 | Langberg et al. |
| 2006/0116756 A1 | 6/2006 | Solem et al. |
| 2006/0116757 A1 | 6/2006 | Lashinski et al. |
| 2006/0184230 A1 | 8/2006 | Solem et al. |

FOREIGN PATENT DOCUMENTS

| | | |
|---|---|---|
| DE | 196 11 755 A1 | 2/1998 |
| EP | 0688545 A1 | 12/1995 |
| EP | 0 727 239 A2 | 8/1996 |
| WO | WO 95/16407 | 6/1995 |
| WO | WO 96/34211 | 10/1996 |
| WO | WO 96/40356 | 12/1996 |
| WO | WO 98/18411 | 5/1998 |
| WO | WO 98/51365 | 11/1998 |
| WO | WO 99/44534 | 9/1999 |
| WO | WO 99/53977 | 10/1999 |
| WO | WO 00/18320 | 4/2000 |
| WO | 00 41649 | 7/2000 |
| WO | WO 00/44313 A1 | 8/2000 |
| WO | 011 00111 | 1/2001 |
| WO | WO 01/50985 A1 | 7/2001 |
| WO | 01 54618 | 8/2001 |
| WO | 01 85061 | 11/2001 |
| WO | WO 01/89426 A1 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/34118 A2 | 5/2002 |

| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/037171 A | 5/2003 |
| WO | WO 2004/084746 A2 | 10/2004 |

OTHER PUBLICATIONS

Liu et al., *Sutural expansion osteogenesis for management of the bony-tissue defect in cleft palate repair: experimental studies in dogs*, PubMed, Excerpt from Plast Reconstr Surg May 2000; 105(6):2012-25; discussion 2026-7, two sheets.

Yoneyama et al., *Super-elastic property of Ti-Ni Alloy for use in dentistry*, PubMed, Excerpt from Front Med Biol Eng 2000; 10(2):97-103, one sheet.

Kotian, *Shape memory effect and super elasticity it's dental applications*, PubMed, Excerpt from Indian J Dent Res Apr.-Jun. 1989; 12(2):101-4, one sheet.

Kuo et al., *The use of nickel-titanium alloy in orthopedic surgery in China*, PubMed, Excerpt from Orthopedics Jan. 1989; 12(1):111-6, one sheet.

Civjan et al., *Potential applications of certain nickel-titanium (nitinol) alloys*, PubMed, Excerpt from J Dent Res Jan.-Feb. 1975;54(1):89-96, one sheet.

Brennan, *Suite of Shape-Memory Polymers*, http:///pubs.acs.org/cen/topstory/7906notw1.html, News of the Week Materials, Feb. 5, 2001, vol. 79, No. 6, Cenear 79 6 pp. 5, ISSN 0009-2347, three sheets.

Stikeman, *Total Recall*, An MIT Enterprise Technology Review—Innovation, Jun. 2001, two sheets.

European Patent Office Office action dated Dec. 22, 2003 for Application No. 00 946 661.6-2310, 4 sheets.

Written Opinion dated Nov. 8, 2002 for International application No. PCT/EP01/10371, 14 sheets.

International Search Report dated Apr. 23, 2002 for International application No. PCT/EP01/10371, 4 sheets.

Internatioanl Search Report dated Mar. 15, 2000 for National application No. SE 9902455-6, 3 sheets.

Internatioanl Search Report dated Oct. 9, 2002 for National applications No. SE 0200073-5, 5 sheets.

International Search Report dated Jun. 5, 2003 for International application No. PCT/EP 02/14655, 7 sheets.

Buchanan et al., Circumferential Suture of the Mitral Annulus for Correction of Mitral Regurgitation in Dogs, Veterinary Surgery, 27: 182-193, 1998.

Buchanan JW, Sammarco CD, Circumferential Suture of the Mitral Annulus for Correction of Mitral Regurgitation in Dogs, PubMed, Excerpt from Vet Surg May-Jun. 1998; 27(3): 182-93, abstract, one sheet.

\* cited by examiner

DELAYED MEMORY DEVICE

TECHNICAL FIELD OF THE INVENTION

The present invention relates to a medical device for providing a change of shape in a part of the body of an organism. The invention further relates to a device and a method for reshaping a body vessel, and a device and a method for restraining growth of a body organ of an organism.

BACKGROUND OF THE INVENTION

At present the treatment of mitral annulus dilatation and other mitral insufficiencies consists of either repair or mitral valve replacements. Both methods require open-heart surgery, by the use of total cardiopulmonary by-pass, aortic cross-clamping and cardioplegic arrest. To certain groups of patients, open-heart surgery is particularly hazardous and therefore a less invasive method for repair of mitral insufficiency is desired.

Such a less invasive method is proposed in U.S. Pat. No. 6,210,432, which describes a method for treatment of mitral insufficiency without the need for cardiopulmonary by-pass and opening of the chest and heart. The method uses a device comprising an elongate body having such dimensions as to be insertable into the coronary sinus, which is a vein that substantially encircles the mitral orifice and annulus and drains blood from the myocardium to the right atrium. The elongate body has two states, in a first of which the elongate body has a shape that is adaptable to the shape of the coronary sinus, and to the second of which the elongate body is transferable from said first state assuming a reduced radius of curvature. Consequently, the radius of curvature of the coronary sinus is reduced. Due to the coronary sinus encircling the mitral annulus, the radius of curvature as well as the circumference of the mitral annulus are reduced. Thus, the described method takes advantage of the position of the coronary sinus being close to the mitral annulus, which makes repair possible by the use of current catheter-guided techniques.

According to one method described in U.S. Pat. No. 6,210,432, a device comprising an elongate stent is used. The elongate stent includes hooks which are arranged to dig into the walls of the coronary sinus, by means of the surgeon retracting a cover sheet from the stent, in order to fix the position of the stent in the coronary sinus. A stabilizing instrument is used for keeping the elongate stent in its first state and then, after the hooks have dug into the walls, releasing it to its second state assuming a reduced radius of curvature. However, the position fixation of the elongate stent in the coronary sinus by means of the hooks might be insufficient, so that the sudden release of the contraction of the elongate stent dislocates it. This dislocation of the device might result in unsatisfactory reduction of the circumference of the mitral annulus.

According to an alternative method described in U.S. Pat. No. 6,210,432 the device comprises three stent sections that are positioned in the coronary sinus and connected by wires. The wires may be manoeuvred from outside the vein system such that the distances between the adjacent stent sections are reduced. Also with this method there is a risk of dislocation of the device, since the surgeon might accidentally move insufficiently fixed stent sections out of their proper position while manipulating them from outside the vein system.

SUMMARY OF THE INVENTION

An object of the present invention is to provide a more secure fixation of a medical device for providing a change of shape in a part of the body of an organism.

A particular object of the invention is to provide a more secure fixation of a device for reshaping a body vessel, as described above.

These and other objects are achieved by a device as defined in any one of claims 1, 17, 26, and 31 and by a method as defined in claim 42.

More particularly, according to one aspect of the present invention, a medical device being insertable into the body of an organism comprises a member having a preferred state of shape, towards which the member by means of inherent forces strives when being in a non-preferred state of shape, and a delay means having a weakenable inherent stiffness to hold the member in the non-preferred state of shape for a period of time after the device is inserted into the body of the organism. The member is by means of said inherent forces arranged to provide a change of shape in a part of the body of an organism, whereas the delay means is arranged to delay the change of shape for a period of time. The time period is determined by how fast the weakening of said inherent stiffness proceeds. By delaying the change of shape this way, the device is allowed to heal on to body tissue of the organism before a change of shape of the device occurs. Which parts of the device that become fixed by the healing process can be determined by means of the design of the device. The normal healing process that occurs in every living organism is thus allowed to provide a well-established fixation of the device. Hence, the present invention provides a more secure fixation of a medical device for providing a change of shape in a part of the body of an organism.

In a preferred embodiment of the invention, said delay means holds said member in a non-preferred state of shape by counteracting the inherent forces of the member. Thus, the delay means is arranged to apply force to the member by means of the inherent stiffness, in order to counteract the inherent shape-changing forces of the member and thereby restrain the member from changing its shape.

Preferably, said delay means holds said member in a non-preferred state of shape while the inherent stiffness of the delay means overcomes the inherent forces of the member. That is, there is an equilibrium between the inherent forces of the member and the inherent stiffness of the delay means, and when the stiffness of the delay means no longer is strong enough to balance the inherent forces of the member, the change of shape will occur.

In another preferred embodiment of the invention, said delay means comprises a decomposable material. In this way, the inherent stiffness of the delay means is allowed to weaken simply as a result of the decomposable material of the delay means being decomposed.

Preferably, said delay means comprises a resorbable material. A resorbable material is a material that when it is inserted into the body of an organism, it will be resorbed by the body by means of enzymatic processes, by active absorption by the cells in the blood and tissue cells of the body, and/or by hydrolysis. Thus, the resorbable material of the delay means will advantageously be decomposed and vanish from the device by time, without leaving any major waste products in the body.

In another preferred embodiment, said member comprises an elastic material. An elastic material can in a simple way be forced to adopt a non-preferred shape.

In yet another preferred embodiment, said member comprises a material having superelasticity properties. Superelasticity properties means that the material may be deformed and in the deformed state the material will use its superelasticity forces to return to its preferred shape. These superelasticity forces thus constitute advantageously at least part of said inherent forces providing said strive towards said preferred state of shape of the member.

Preferably, said member comprises a shape memory material. A shape memory material is a material that has two different forms, one at lower temperatures and another at higher temperatures. At the lower temperatures, e.g. below 30° C., the material is elastic and may be introduced into the body. At the higher temperatures, the material is still elastic but becomes also superelastic and assumes its preferred original shape unless the transformation to this original shape is obstructed by external stress to the material. The use of a shape memory material in the member is advantageous inter alia because then one can easily provide the device with said delay means while the member, at a lower temperature outside the body, more easily remains in a shape corresponding to said non-preferred state of shape inside the body.

According to another aspect of the present invention, a medical device for providing a change of shape in a part of the body of an organism comprises a first set of forces working towards a change of shape of the device, and a second set of forces working for preserving a present shape of the device and thereby counteracting said first set of forces. Said first and said second sets of forces are each inherent in a solid material of the device, and the forces of said second set of forces are arranged to decrease as a result of said solid material interacting chemically with said part of the body. As a result of the chemical interaction between the solid material of the device and the surrounding body, the forces of the second set of forces decrease and thus allow the device to provide said change of shape after a while, when parts of the device have become fixed in the body by a healing process. An advantage of the present invention, except that it provides a more secure fixation, is that there is no need for a stabilizing surgical instrument for keeping a present shape of the device during operation, since the shape is preserved by means of said second set of forces being inherent in the device itself.

Preferably said second set of forces is inherent in a decomposable material as mentioned above.

Said forces of said second set of forces are preferably arranged to decrease as a result of said solid material being decomposed by said part of the body.

In a preferred embodiment of the invention, said second set of forces is inherent in a resorbable material as described above.

Preferably, said forces of said second set of forces are arranged to decrease as a result of said solid material being resorbed by said part of the body.

In another preferred embodiment, said first set of forces is inherent in an elastic material.

Preferably, said first set of forces is inherent in a material having superelasticity properties as described above.

Said first set of forces is preferably inherent in a shape memory material as also described above.

In one embodiment of the invention, said first set of forces is inherent in a shape memory metal.

In an alternative embodiment of the invention, said first set of forces is inherent in a shape memory polymer.

The device is in one embodiment arranged to contract into a new shape as a result of said second set of forces being decreased.

In an alternative embodiment, the device is arranged to expand into a new shape as a result of said second set of forces being decreased.

The device could be arranged to change its shape in one dimension only, but it could also be arranged to change its shape in two dimensions, or even in three dimensions.

According to yet another aspect of the present invention, a medical device being insertable into the body of an organism comprises a member having a preferred state of shape and having a tendency to transfer its shape towards said preferred state of shape when being in a non-preferred state of shape. The device further comprises a resorbable means being arranged to hold the member in the non-preferred state of shape and to delay the transfer when the device is inserted into the body of the organism by counteracting said transfer during resorption of the resorbable means by the surrounding body of the organism. The resorption of the resorbable means by the surrounding body makes the resorbable means gradually vanish. Thus, after some period of time when parts of the device have grown on to body tissue, there is nothing left to hold the member in the non-preferred state of shape, whereby said transfer is released.

Also according to this aspect of the invention, said member preferably comprises an elastic material.

Preferably, said member comprises a material having superelasticity properties.

It is also preferred that said member comprises a shape memory material.

According to a particular aspect of the present invention, a device for reshaping a body vessel is elongate and has such dimensions as to be insertable into the vessel and has two states, in a first of which the device has a shape that is adaptable to the shape of the vessel, and to the second of which the device is transferable from said first state. The device further comprises a fixing means for fixing the ends of the device within the vessel, when the device is first positioned therein, a member for transferring the device to the second state by reshaping it, and a resorbable means for delaying said reshaping until the ends of the device are fixed by keeping said device in said first state until the resorbable means is resorbed. By allowing the ends of the device to heal on to the walls of the vessel, e.g. the coronary sinus, by means of said fixing means, before said reshaping of the device occurs, the present invention provides a more secure fixation of a device for reshaping a body vessel.

Preferably, said resorbable means comprises a resorbable sheath being arranged to enclose said member. This is advantageous since with the shape of a sheath the resorbable means is both easy to manufacture and easy to arrange on the member.

In another preferred embodiment of the invention, said fixing means is arranged to expand against the wall of the vessel when first positioned therein. This expansion against the wall of the vessel initiates and contributes to the fixing of the ends of the device, thus enabling a rigid fixing.

In yet another preferred embodiment of the invention, said fixing means is arranged to grow into the wall of the vessel. By taking advantage of the healing process in the tissue of the vessel wall, the fixing means can be fixed effectively. This can be facilitated by an expansion against the wall of the vessel as mentioned above.

In a preferred embodiment, said fixing means comprises a self-expandable stent at each end of the device.

According to another preferred embodiment, said member comprises a shape memory material providing said reshaping of the device.

Preferably, said reshaping of said device comprises shortening of said device.

In another preferred embodiment, said device is used for treatment of mitral annulus dilatation. Since the device can be inserted into a body vessel using catheter-guided techniques, the use of this device for treatment of mitral annulus dilatation is advantageous compared to open-heart surgery, which is the present procedure for repairing or replacing the mitral valve.

In yet another preferred embodiment, said vessel is the coronary sinus. The coronary sinus encircles the mitral orifice and annulus. Therefore, a reshaping of this vein also has a compressing effect on the mitral annulus.

Preferably, said reshaping of said device is used for reducing the radius of curvature of the coronary sinus. Hence, the radius of curvature as well as the circumference of the mitral annulus are also reduced. According to the invention, a method for reshaping a body vessel comprises the steps of inserting a device into the vessel, fixing the ends of the device within the vessel, reshaping the device, and delaying said reshaping by a resorbable means so that the step of fixing the ends of the device is performed before the step of reshaping the device.

According to a preferred embodiment, said step of fixing the ends of the device comprises providing a growth of the ends into the wall of the vessel.

According to another preferred embodiment, a shape memory material is used in the device for said step of reshaping the device.

Preferably, Nitinol is used in the device for said step of reshaping the device.

In a preferred embodiment, said step of reshaping the device comprises the step of shortening the device.

In another preferred embodiment, the method is used for treatment of mitral annulus dilatation.

In yet another preferred embodiment, said device is inserted into the coronary sinus in the vicinity of the posterior leaflet of the mitral valve.

Preferably, said reshaping is used for reducing the curvature of the coronary sinus and thereby reducing the radius of circumference of the mitral valve annulus.

The basic inventive idea, that reshaping of an implantable device may be delayed by means of a delay means being comprised in the device itself, opens up for new possibilities within many medical applications.

The present invention could be used for instance when a delayed expansion of a stent is desired. The stent could then preferably be crimped to a small diameter by means of a resorbable suture or, alternatively, a resorbable film. The film or thread would slowly be eaten away and the shape-changing forces may be released after the desired delay which is programmed in the properties of the resorbable restraining material. Such a stent might be used inside vessels, the trachea, the biliary tract or any other hollow structure in the human or animal body.

The invention would also be useful where openings of human, or animal, organs or other structures need to be opened or closed slowly. For instance, when an opening between the left and right side of the heart is present, an immediate closure of the opening could be dangerous, whereas a slower closure would be tolerated.

Within many medical areas, the present invention would be useful when a continuous long-term effect of shape-changing forces is desired. One such application would be a device designed to shorten or lengthen a human or animal structure in one or more dimensions. The device according to the invention would then have time to heal into the body structure before shape-changing forces are released and force the body structure to slowly change its shape.

This could for example be useful in the area of orthopaedics for lengthening of a bone structure.

For orthodontic treatment, the described invention would be useful when it comes to tooth-regulation and lengthening of the maxilla and/or mandibula, i.e. the upper and lower jaws.

In plastic surgery an extra growth of skin area is often used to cover skin defects. Using the present invention a slow growth of skin area would be augmented.

An example within the area of urology surgery is lengthening of a penis. In this case a device made of three segments could be designed, where the distal ends of the device first are allowed to grow into the tissue. After fixation of the two ends of the device in the penis tissue, the mid portion which temporarily has been restrained by means of a resorbable material as described above will be released and the mid portion of the device will grow in length. One specific capacity of a human or animal body is to allow slow deformation of organs or tissues by compensatory tissue adaptation. A penis would therefore grow slowly to a predetermined length.

By means of the present invention, a sequential effect of shape-changing forces could also be provided, i.e. change of shape could occur in two or several steps as a result of resorbable material releasing the shape-changing forces in predetermined steps. In each step, a part or parts of a device could first heal into a body structure and secondly the desired shape-changing effects could be released.

As seen from the examples above, a substantial advantage of the present invention is that a change of shape is allowed to be made slowly so that body tissues have time to adapt.

Other medical applications of particular interest, which could be improved by using the present invention, are treatment of pathological heart growth and treatment of pathological alveolar sac growth. Some background of these two diseases will be given next.

Dilated cardiomyopathy (DCM) and ischemic heart disease (IHD) are common reasons for heart failure (HF). Heart failure in its terminal status is a deadly disease, and it is by far the most common cause of death in most countries, developed and undeveloped. Progressive HF, when it is deteriorating, results in a growth in the diameters of the heart ventricles, thus resulting in a general heart growth. The growth in heart size by dilatation initiated by myocardial pathology creates itself by its increase in heart diameter a pathology of its own, in the way of functional disorders.

Dr. Randas Batista implemented a surgical treatment for this disease by resecting big parts of the left ventricle (LV) with or without repair of the mitral valve. The long time results were, however, dismal since the LV tends to dilate again a second time despite of having been reduced in size by surgery (see Kawaguchi, A. T. et al. "Mitral Regurgitation Redilates the Left Ventricle After Partial Left Ventriculectomy (Batista Operation)." Journal of the American College of Cardiology, February 1998, Vol.31, No.2, Suppl.A, page 376A, ISSN: 0735-1097; see also Kawaguchi, A. T. et al. "Intraoperative Left Ventricular Pressure-Volume Relationship in Patients Undergoing Left Ventricular Diameter Reduction." Circulation, 1997, Vol.96, No.8, Suppl., page 1198, ISSN: 0009-7322; and Pérez de la Sota, E. et al. "Early Results with Partial Left Ventriculectomy (the Batista Operation)." Revista Espanola de Cardiologia, August 2000, Vol.53, No.8, pages 1022–1027, ISSN: 0300-8932).

Supporting the LV and preventing progressive LV dilatation in HF actively by means of wrapping the heart with living skeletal muscle from the back of the patient, stimulated by pacemaker, was introduced by Dr. Carpentier in the eighties (Chachques, J. C. et al. "Dynamic Cardiomyoplasty: clinical follow-up at 12 years." European Journal of Cardio-Thoracic Surgery: Official Journal of the European Association for Cardio-Thoracic Surgery, October 1997, Vol.12, No.4, pages 560–568, ISSN: 1010-7940). The method has been rarely used and its effectiveness has been questioned.

More recently, methods of restraining the heart from growing have been introduced by Acorn Cardiovascular, Inc, St. Paul, Minn., USA. They are supporting the heart by means of a polyester mesh sutured to the surface of the heart after exposing the heart by splitting the sternum and opening the pericardium.

Even reducing the LV diameter by force, using wires that transverse the LV cavity and subsequent fixation, has been introduced by Myocor, Maple Grove, Minn. 55311, USA.

Chronic obstructive pulmonary disease (COPD) is an umbrella term used to describe airflow obstruction that is associated mainly with emphysema and chronic bronchitis. COPD is the fourth leading cause of death in the U.S. in 1998, according to the National Center for Health Statistics, Report of Final Morbidity Statistics, 1998. Emphysema causes irreversible lung damage by weakening and breaking the air sacs within the lungs. Further, sick air sacs sometimes grow unrestrainedly and repress smaller air sacs, resulting in lack of oxygen and by time death. This disease is hard to treat. At present, surgical treatment of dilated air sacs involves cutting them away, but this treatment gives no long-term effect since a new air sac will soon start to grow.

All these known methods for treatment of pathological heart growth and said known method for treatment of alveolar sac growth require, whether they are effective or not, major heart or lung surgery which, as mentioned before, is particularly hazardous to certain groups of patients. Therefore less invasive methods for treatment of pathological heart growth and alveolar sac growth are desired as well.

It is an object of the present invention to also provide less invasive treatments of pathological growth of body organs, by which treatments more long-term effects can be achieved.

A particular object of the invention is to provide less invasive treatments of pathological heart growth and alveolar sac growth.

These further objects are achieved by a device as defined in claim 50 and by a method as defined in claim 53.

More particularly, according to a further aspect of the present invention, a device for restraining growth of a body organ of an organism is implantable into the body of the organism and comprises an elastic contractable member being arranged to enclose said body organ, and a resorbable means being arranged to delay contraction of the contractable member when the device is implanted in the body of the organism by counteracting the contraction during resorption of the resorbable means by the surrounding body of the organism.

A basic advantage of the device according to the invention is that the device, since said contractable member is elastic, can be inserted into the body using catheter-guided techniques. Hence, less invasive treatments can be provided.

Another advantage, which comes both from the elasticity and the delayed contraction, is that the device can be inserted by means of catheter-guided techniques even if said contractable member comprises a large area. This is due to the fact that the substantially elastic device at the insertion can be rolled up on a catheter and then be unfolded to enclose said organ.

After a period of time after the surgical or percutaneous insertion, the device will start to contract as a result of the resorbable means being resorbed. The contraction will then make the device enclose the organ tight and apply a restraining force which holds back the growth of the organ. Since the implanted device applies a continuous restraining force to the organ, more long-term effects can be achieved in treatment of growing body organs. It is to be noted that if the contraction of the device would not have been delayed, it would have been very difficult to roll up the device on a catheter and then unfold it round the organ.

Preferably, said contractable member comprises a shape memory material.

According to the invention, a method for restraining growth of a body organ of an organism comprises the steps of inserting a restraining device into the body of the organism, enclosing at least partly the body organ with the restraining device, compressing said restraining device by means of a contractable member of said restraining device, and delaying said compression by a resorbable means.

This inventive method could be used not only for treatment of pathological heart growth and alveolar sac growth, but also for treatment of bullous emphysema and for treatment of other body organs growing pathologically.

A device according to the present invention may be fixed in body tissue by other means in combination with or instead of the healing process allowed by the delaying of the change of shape. Hence, fixing of a device according to the invention may as well be accomplished for example by means of suturing, gluing, clipping or using hooks. These means of fixation would permit a better healing in of the device in the tissue and also prohibit dislocation while healing in.

As already seen, the number of advantages of the inventive device is large, of which a few are mentioned next. The present invention allows:

1. less invasive surgical treatments;
2. devices that are properly fixed inside the body by means of parts healing into the body tissue;
3. devices to be designed that have multiple purposes;
4. eliminating stabilizing surgical instruments for keeping a present shape of the device during operation;
5. engineering to decide when a shape-changing action by the device is to take place in the body;
6. a change of shape to be made slowly so that body tissue has time to adapt.

It should be understood that many modifications are possible within the spirit and scope of the invention, which is only limited by the appended claims. A few applications of the invention are mentioned above, of which some will be further described by way of illustration only in the detailed description. However, many other medical areas where the invention might be used will become apparent to those skilled in the art.

BRIEF DESCRIPTION OF THE DRAWINGS

The invention will now be described in more detail with reference to the accompanying drawings, in which

FIG. 16 is a schematic view illustrating the second state of a device according to FIG. 14 or 15a;

DETAILED DESCRIPTION OF PREFERRED EMBODIMENTS

FIGS. 1 to 4 show the principle of delayed shortening according to the invention.

Figure 1:
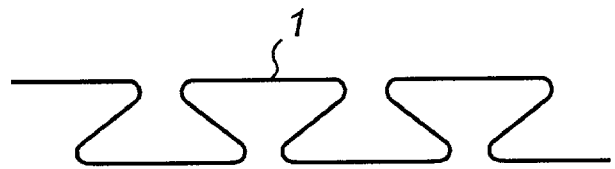
FIGS. 1–4 are schematic views of the structure and the operation of an embodiment of a device according to the invention, illustrating the principle of delayed shortening.

In FIG. 1, a shape-changing member 1, here in the form of a thread 1, made of or at least in part including a shape memory material is shown having a curved shape. This shape is the original shape that the shape-changing member 1 "remembers" and will assume when the temperature thereof passes a certain threshold, e.g. exceeds 30° C.

Figure 2:
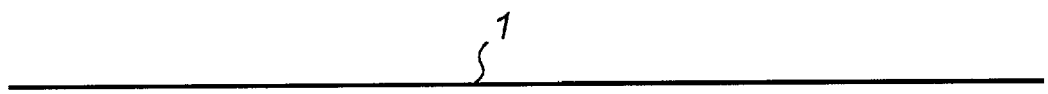

FIG. 2 shows the shape-changing member 1 of FIG. 1 having been straightened by stretching to a substantially straight shape.

Figure 3:
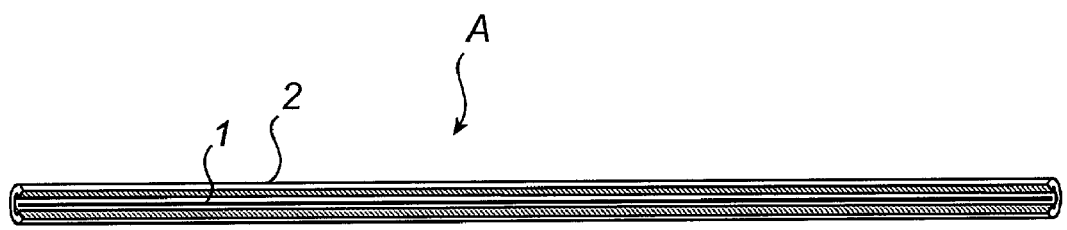

FIG. 3 illustrates an embodiment of a device according to the invention, where the device is in its non-activated state of shape A. More specifically, by covering the stretched and straight shape-changing member 1 in FIG. 2 with a delay means 2, here in the form of a tube 2 having a sufficiently small inner cross-section, the stretched shape of the shape-changing member 1 can be maintained even when the device is implanted into a human body and the temperature of the shape-changing member 1 thus exceeds the threshold, e.g. 30° C.

The delay means 2 may be flexible enough to follow the curves in e.g. vessels, but has a stiffness, here especially in its radial direction, which withstands the shape-changing force of the shape-changing member 1. Thus, having been implanted into the human body, the shape-changing member 1 of the device will strive towards its original, here curved, shape according to FIG. 1, but is restrained by the delay means 2.

Figure 4:
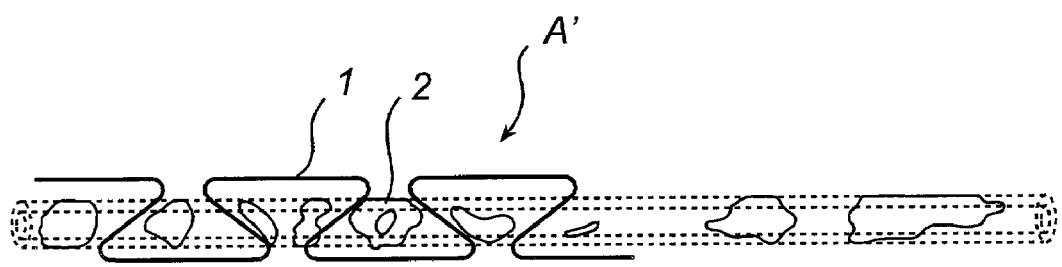

However, by manufacturing the delay means 2 from a resorbable material, the delay means 2 will be resorbed by time and the shape-changing member 1 will resume its original shape when the delay means 2 has been resorbed to such a degree or extent that it cannot restrain the shape-changing member 1 any longer, as schematically illustrated in FIG. 4. Thus, the device has now "been transformed" from its non-activated long state of shape A (FIG. 3), to an activated, shortened state of shape A' (FIG. 4), where the device consists essentially of the shape-changing member 1 only.

The device in FIG. 3 may be manufactured in the following way. The thread 1 of a shape memory material, e.g. with the shape illustrated in FIG. 2, is programmed to remember the shape illustrated in FIG. 1 by being held in that shape while at the same time being heated to a temperature above said threshold. Upon cooling, beneath the threshold temperature, e.g. down to room temperature, the thread 1 will become more flexible and may more easily be deformed into its previous shape shown in FIG. 2. In this cooled state, the thread 1 is covered by the resorbable tube 2, e.g. by threading the tube 2 onto the thread 1 or by forming the tube 2 around the thread 1. Other embodiments of a device according to the invention may operate and may be manufactured in a corresponding manner. Thus, a shape-changing member of a memory material is first held in a "preferred" state of shape while being heated above a threshold temperature, and then cooled beneath the threshold temperature so that it can easily be deformed into its previous "non-preferred" state of shape. Thereafter, the now "programmed" shape-changing member is "locked" in said non-preferred state of shape by a delay means in such a way that the delay means will obstruct the shape-changing member from resuming its preferred state of shape when being heated again, e.g. in a human body. Referring again to FIG. 3, the inner radius of the tube 2 must not necessarily be so small that the shape-changing member in the form of the thread 1 cannot move at all in the radial direction. Hence, there may be a small radial play in which the shape-changing member 1 can move without consequently being able to change the length of the device to any larger extent. However, the device in FIG. 3 may also be manufactured with essentially no play between the shape-changing member 1 and the inner side of the delay means 2, possibly also with a pretension or bias force from the delay means 2 acting on the shape-changing member 1.

In order to clearly illustrate the shortening of the device, the curved thread 1 is located to the left in FIG. 4, but, after its transformation, the thread 1 may just as well be located anywhere along the remaining parts of the tube 2.

FIGS. 5 to 8 show the principle of delayed elongation according to the invention.

Figure 5:
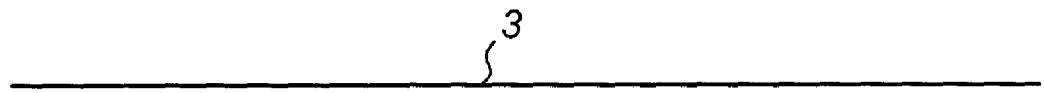
FIGS. 5–8 are schematic views of the structure and the operation of another embodiment of a device according to the invention, illustrating the principle of delayed elongation.

In FIG. 5, a shape-changing member 3, here in the form of a thread 3 of a shape-memory material, is shown having a straight original shape.

Figure 6:
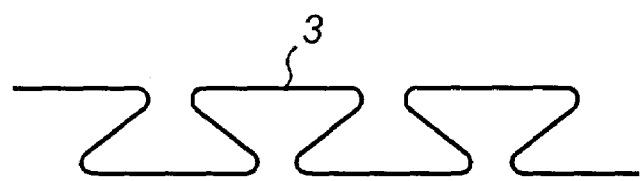

FIG. 6 shows the shape-changing thread member 3 of FIG. 5 when having been folded to a curved shape.

Figure 7:
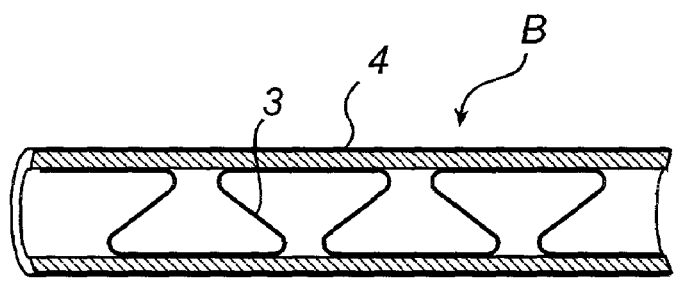

FIG. 7 illustrates an embodiment of a device according to the invention comprising a thread as illustrated in FIG. 6, where the device is in its non-activated state of shape B. By covering the curved shape-changing member 3 with a delay means 4 in the form of a tube 4 of a resorbable material, the curved shape B can be maintained even when the device is implanted into a human body and strives towards its original straight shape.

Figure 8:
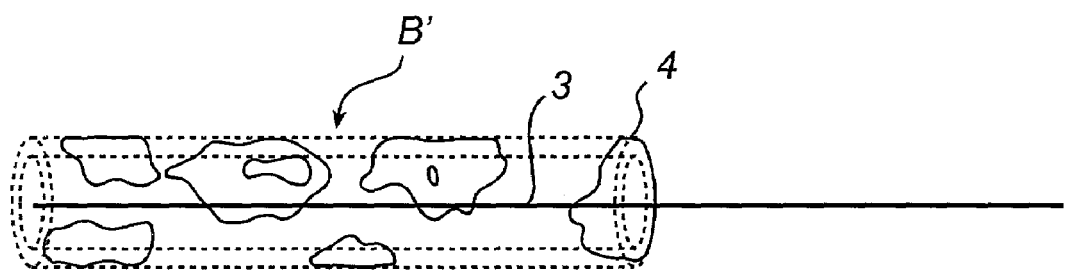

As schematically illustrated in FIG. 8, after implantation into the human body, the delay means 4 is resorbed by time and consequently the shape-changing member 3 will be released to resume its original straight shape B'. Thus, the device has now been transformed from its non-activated short state of shape B (FIG. 7) to an activated, elongated state of shape B' (FIG. 8).

In the illustrated embodiments, the length of the shape-changing member 1;3 is substantially unchanged by the transformation, whereas the shape of the shape-changing member 1;3 is changed so that the length of the device is changed.

According to the invention, the material from which the shape-changing member is made may consist of or at least include Nitinol, which is an alloy composed of nickel (54–60%) and titanium. Small traces of chromium, cobalt, magnesium and iron may also be present in Nitinol. Alternatively, other materials such as Shape Memory Polymers (SMP) could be used as the shape memory material.

Actually, as far as the present invention concerns, the shape-changing material does not have to be a shape memory material. Any superelastic material would function in most applications. For example stainless steel (and other metals) may also be forced into a non-preferred state of shape by means of a resorbable restraining means.

Examples of usable resorbable materials from which the delay means may be made, or that are at least included, are PDS (polydioxanon), Pronova (polyhexaflouropropylen-VDF), Maxon (polyglyconat), Dexon (PGA, polyglycolic acid), Vicryl (polyglactin), PLA (polylactic acid), PDLLA (polydexolactic acid), PLLA (pololevolactic acid), starch, different kinds of sugar, butyric acid, collagen, and collatamp.

Depending on the choice of material, the release of the shape-changing forces may be delayed for a desired period of time. Also design parameters such as the thickness of the resorbable material may be set so that the shape-changing forces are delayed as long as desired. The delay time may vary from e.g. a few days up to several years depending on the application.

The thickness of the delay means may vary along the device, so that the order in which different parts of the device are released by the delay means may be controlled.

FIGS. 9 to 20 show some different embodiments of a device according to the invention.

Figure 9:
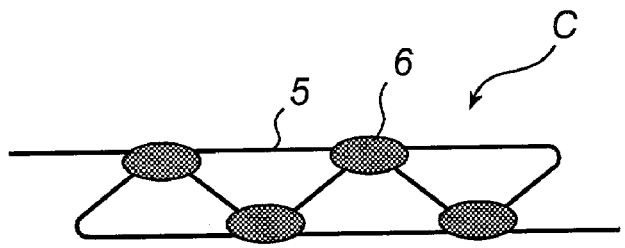
FIG. 9 is a schematic view of another embodiment of a device according to the invention being an alternative to the embodiment shown in FIG. 7.

FIG. 9 shows an embodiment of a device according to the invention being an alternative arrangement of a device for delayed elongation as compared to the device shown in FIG. 7. Instead of a resorbable tube 4 as in FIG. 7, the resorbable means comprises resorbable crosslinks 6 which hold the shape-changing member 5 in its curved state of shape and thus the device in its non-activated short state of shape C.

Resorbable crosslinks 6 (FIG. 9) may also be combined with a tube 4 (FIG. 7).

Figure 10:
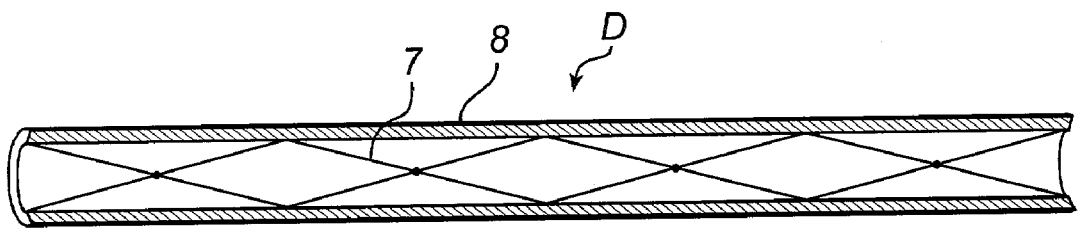
FIGS. 10 and 11 schematically illustrate another embodiment of a device according to the invention, shown in a first state and a second shortened state, respectively.
Figure 11:
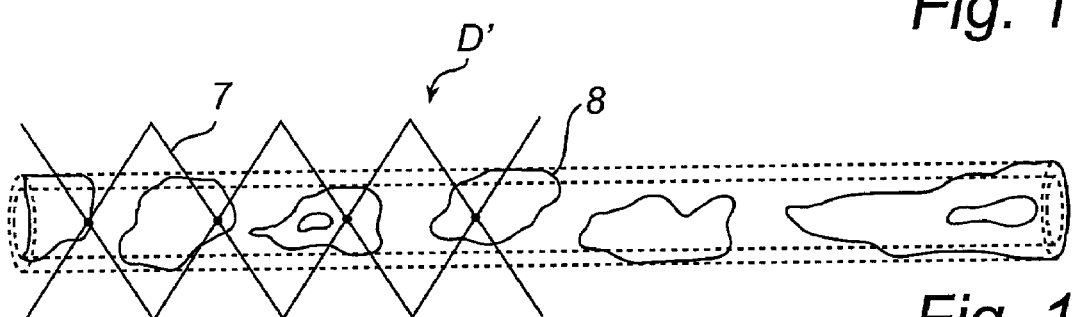

FIG. 10 shows an embodiment of a device according to the invention in its non-activated elongate state of shape D. Here, the shape-changing member 7 is scissors-shaped. A delay means 8 in the form of a tube 8 of resorbable material holds the shape-changing member 7 in a stretched, elongated state of shape and, thus, also the device in its elongate state of shape D. When the delay means 8 has been sufficiently resorbed, the scissors-shaped shape-changing member 7 will resume its original non-stretched shape and the device is transformed to its activated short state of shape D' (FIG. 11).

Figure 10A:
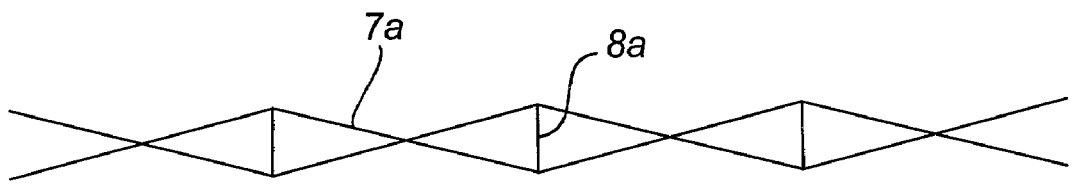
Figure 11A:
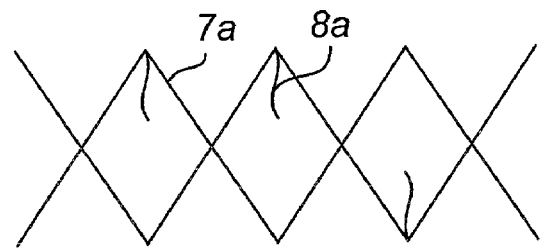

FIG. 10a shows an alternative embodiment of a device according to the invention, where the tube 8 in FIG. 10 is replaced by a delay means in the form of resorbable threads 8a. The delay means 8a holds the scissors-shaped shape-changing member 7a in a stretched, elongate state of shape and, thus, the device in a state of shape corresponding to D in FIG. 10. Referring to FIG. 11a, when the delay means 8a is cut off by means of resorption, the shape-changing member 7a will resume its original non-stretched shape and the device is transformed to its activated short state of shape corresponding to D' in FIG. 11.

Figure 12:
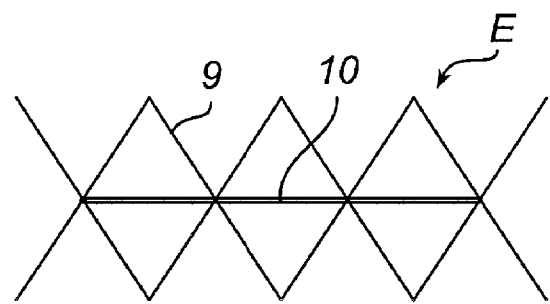
FIGS. 12 and 13 schematically illustrate another embodiment of a device according to the invention, shown in a first state and a second elongated state, respectively.
Figure 13:
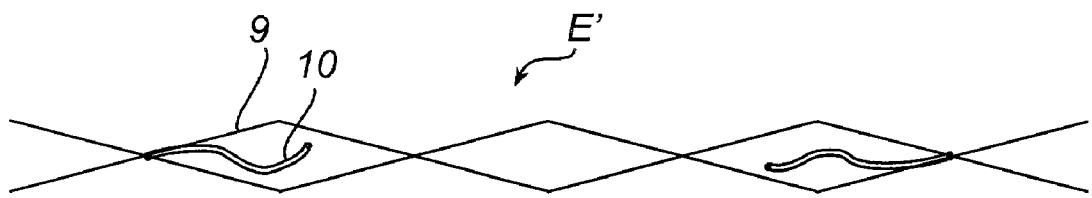

FIG. 12 shows an embodiment of a device according to the invention in its non-activated short state of shape E. A scissors-shaped shape-changing member 9 of the device is held in a short state of shape by means of a delay means in the form of a resorbable thread 10, and, thereby, the whole device is held in its short state of shape E. When the delay means 10 is cut off by means of resorption, the shape-changing member 9 will resume its original elongate shape so that the device is transformed to its activated state of shape E' (FIG. 13).

Figure 14:
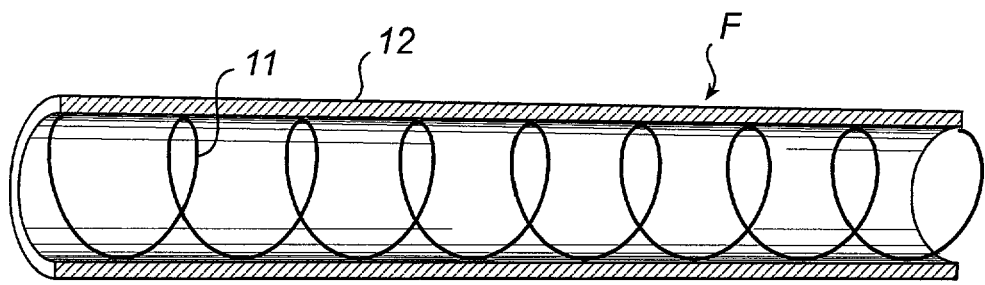
FIG. 14 is a schematic view of yet another embodiment of a device according to the invention, shown in a first state.
Figure 16:
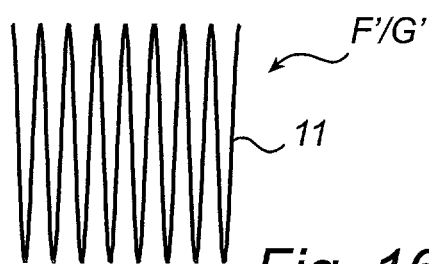

FIG. 14 shows an embodiment of a device according to the invention comprising a shape-changing member in the form of a coil 11 of a shape-memory material having been stretched and arranged in a delay means in the form of a tube 12 of resorbable material. The device is then in its non-activated state of shape F. When the delay means 12 has been sufficiently resorbed, the shape-changing member 11 will resume its original shorter and wider shape as shown in FIG. 16, and the device is transformed to its activated state of shape F'.

Figure 15A:
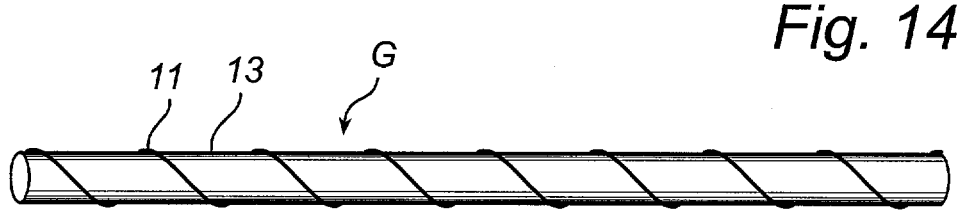
FIG. 15a is a schematic view of another embodiment of a device according to the invention being an alternative to the embodiment shown in FIG. 14 and being shown in a first state.
Figure 15B:
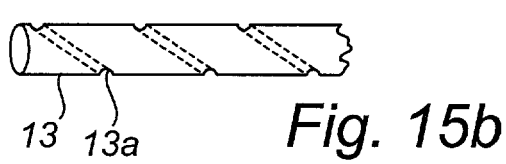
FIG. 15b is a schematic view of a device according to FIG. 15a, illustrating the structure of a part of the device.

In an alternative embodiment shown in FIGS. 15a and 15b of a device according to the invention, the tube 12 in FIG. 14 is replaced by a resorbable rod 13 provided with grooves 13a in which a coil 11 is initially wound. The winding of the coil 11 in the grooves 13a obstructs the coil 11 from resuming its original shape (FIG. 16) and, hence, the device is held in its non-activated state of shape G by the rod 13, as illustrated in FIG. 15a. By resorption of the rod 13 in e.g. a human body, the shape-changing force of the coil 11 is released and the device is transformed to its activated state of shape G' as shown in FIG. 16.

Figure 17:
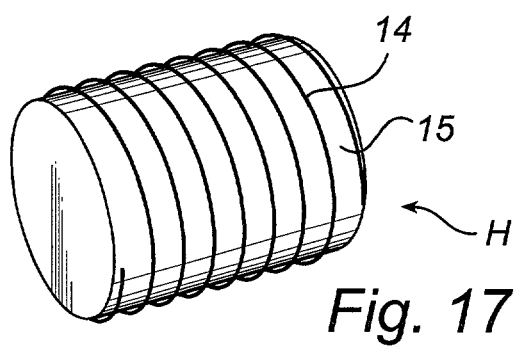
FIGS. 17 and 18 are schematic views illustrating another embodiment of a device according to the invention, shown in a first state and a second state, respectively.
Figure 18:
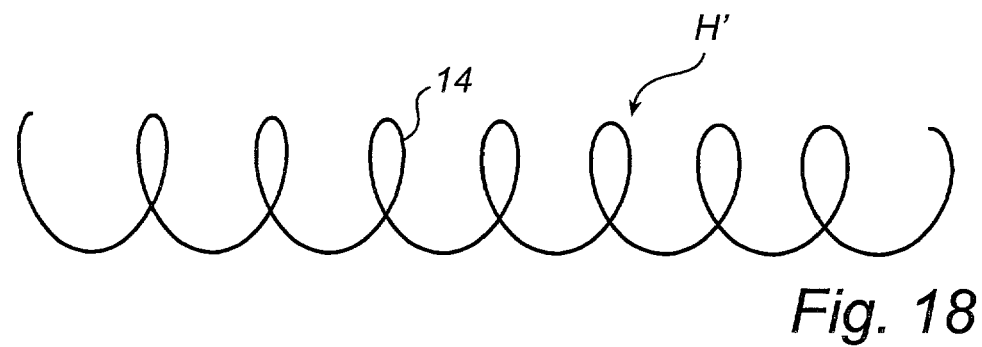

In another embodiment shown in FIG. 17 of a device according to the invention, a coil 14 is wound around a resorbable rod 15. When the rod 15 is resorbed, the shape-changing forces of the coil 14 will be released so that the coil 14 resumes an original elongate shape, as shown in FIG. 18, whereby the device is transformed from its non-activated state of shape H to its activated state of shape H'.

Figure 19:
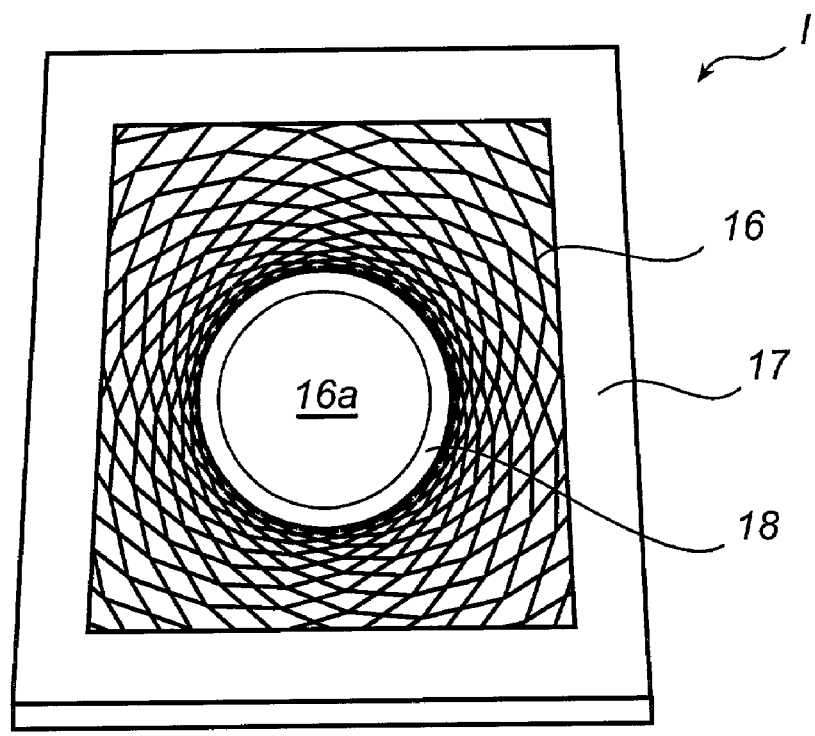
FIG. 19 is a schematic perspective view of a device for two-dimensional contraction according to the invention.

FIG. 19 shows an embodiment of a device according to the invention in the form of a patch for closing or obstructing openings, e.g. in the heart of a human or animal body. The patch has a shape-changing member 16 comprising a grid matrix formed by threads made of memory material such as Nitinol or SMP. The threads may be covered individually by biocompatible material such as PTFE or dacron to fill in the gaps between the threads, e.g. in the way shown in FIG. 26 with threads 28 and biocompatible material 29.

The patch in FIG. 19 further comprises a frame 17 for anchoring the patch in the body, e.g. by means of sutures. The frame may be made of any biocompatible material, such as PTFE or dacron. By the use of a cone (not shown), the threads may be spread apart, creating a central opening 16a in the patch. The cone is advanced until a delay means 18 in the form of a separate ring 18 of a resorbable material, initially positioned on the cone, is positioned in the opening 16a. The cone is then drawn back and the ring 18 is left in the opening 16a, restraining the elastic threads in such a way that the central opening 16a in the patch is maintained. FIG. 19 shows the patch in its non-activated state of shape I with the ring 18 positioned centrally. After implant and sufficient resorption of the restraining ring 18 and after a specified period of time, the central opening in the patch is closed and the patch is activated.

Figure 20:
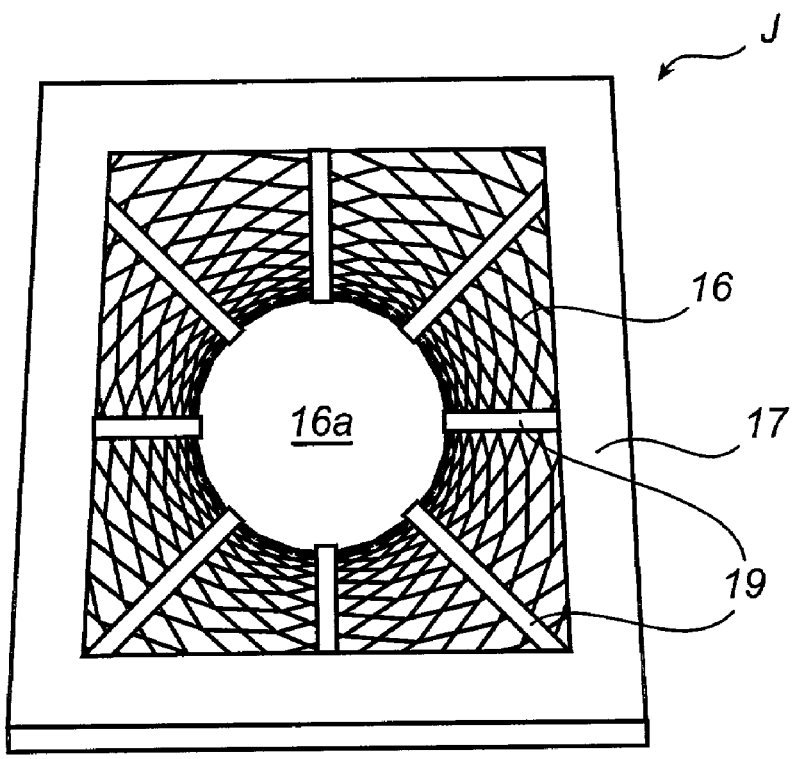
FIG. 20 is a schematic perspective view of another device for two-dimensional contraction according to the invention.

FIG. 20 shows an alternative embodiment of a device according to the invention in the form of a patch for closing openings. The patch may be constructed by attaching delay means 19 in the form of resorbable threads or bands 19 to the top of a sharp cone and down along the sides of the cone, advancing the cone through the middle of the patch so that the elastic threads 16 are spread out and thus an opening 16a in the patch is created, and fastening one end of each band to the frame 17 on one side of the patch and the other end of each band 19 to the frame 17 on the other side of the patch, so that each band 19 encircles the opening. The bands 19 could be placed at regular intervals along the circumference of the opening so that they expand a substantially circular hole in the middle of the patch. By means of the resorbable bands 19, the patch is held in its non-activated state of shape J.

It is to be noted that the above-described different embodiments are examples only. There are many possible different forms of a device according to the present invention. For example, the single shape-changing thread in FIGS. 1 to 9 may be replaced by several threads or by one or more bands. The scissors-shaped members 7 and 9 in FIGS. 10 to 13 may be multiplied so as to form a scissor-shaped area, which in turn may be shaped into different forms. The single tube in FIGS. 3, 7, 10 and 14 may be slotted or may be divided into several tube segments. A delay means may also be provided in the form of resorbable glue, which holds parts of the shape-changing member together and in that way delay the change of shape of the device. The number of possible designs of a device according to the invention is, in fact, infinitely great.

Next, an embodiment according to the invention of a device for treatment of mitral annulus dilatation will be described.

Figure 21:
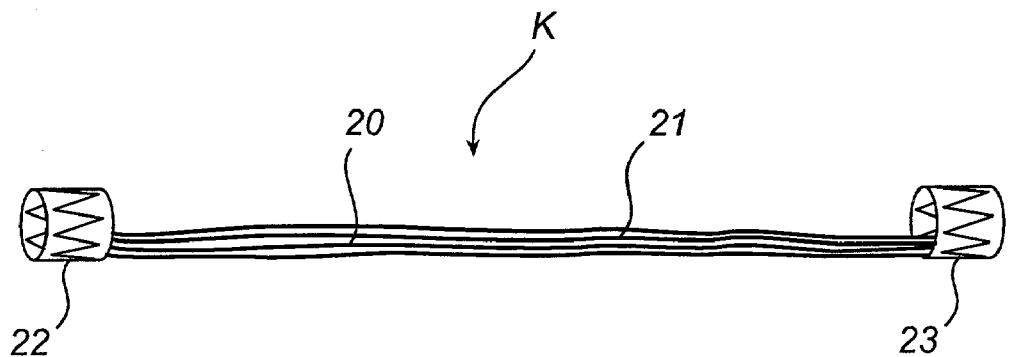
FIGS. 21 and 22 schematically illustrate an embodiment of a device according to the invention for treatment of mitral annulus dilatation, shown in a first state and a second shortened state, respectively.

The device shown in FIG. 21, being in an elongate and non-activated state of shape K, comprises a shapechanging member 20 in the form of a shape memory metal thread 20, a delay means 21 in the form of a resorbable sheath 21 enclosing the shape memory metal thread 20 for holding it in a straightened state of shape, and preferably self-expandable stents 22 and 23 located at the opposite ends of the device.

The device may include one or more additional shape memory metal threads, e.g. if a stronger shortening force is desired.

Figure 22:
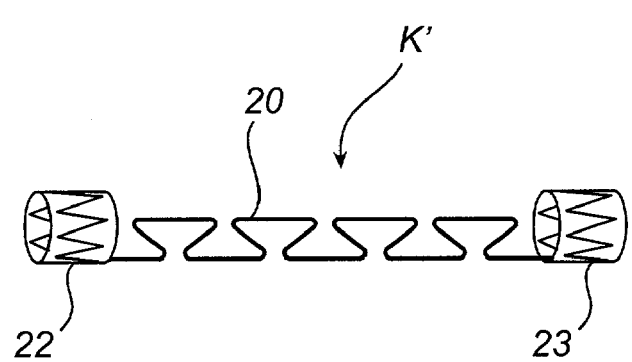

The shape memory metal thread 20 may be made of Nitinol, or other similar material which has a memory of an original shape as illustrated in FIG. 22, and can be temporarily forced into another shape, e.g. as illustrated in FIG. 21.

The resorbable sheath 21 is made of PDS, but it may also be made of any other material which is resorbable by the surrounding blood and tissue when applied in a human body and has the required stability and bending properties. The thickness of the resorbable sheath 21 is chosen so that the time needed for the surrounding blood and tissue in the coronary sinus 24 to resorb the resorbable sheath 21 enough for the device to enter its second shorter state of shape K' is adapted to the time needed for the ends of the device to be fixed within the coronary sinus 24.

Figure 21A:
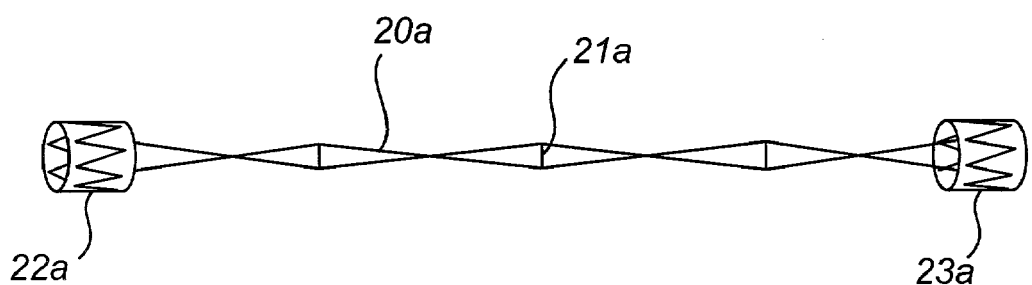
Figure 22A:
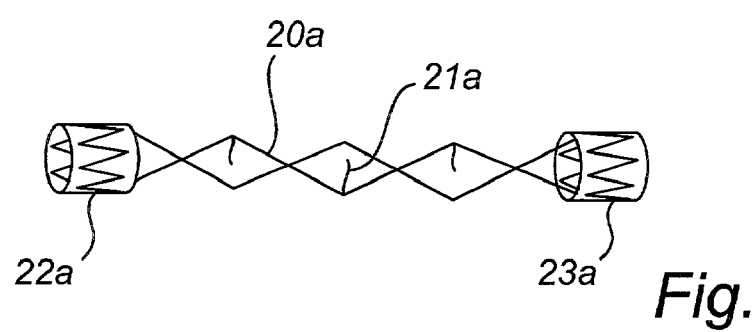

The self-expandable stents 22 and 23 may be of conventional type with an elastic cylindrical unit, made of e.g. Nitinol, in an opened zigzag configuration. FIG. 21a shows an alternative embodiment according to the invention of a device for treatment of mitral annulus dilatation. Here, the shape memory metal thread 20 is replaced by a scissors-shaped shape-changing member 20a. The resorbable sheath 21 may then be replaced by resorbable threads 21a, like in FIG. 10a. Preferably, self-expandable stents 22a and 23a are located at the opposite ends of the device. The state of shape corresponding to K' in FIG. 22 of the device shown in FIG. 21a is shown in FIG. 22a.

Figure 23:
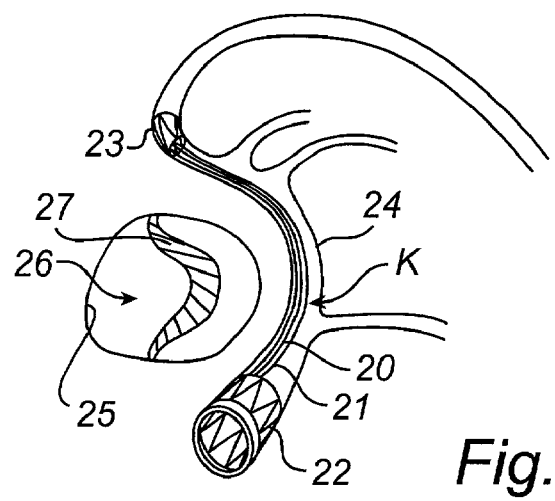
FIGS. 23, 24 and 25 are schematic views illustrating the positioning, the fixing and the shortening respectively, of a device according to FIG. 21 when used in the coronary sinus.

The above-described device as seen in FIG. 21 (or the device as seen in FIG. 21a), is positioned in the coronary sinus 24, shown in FIGS. 23 to 25, in the following way:

An introduction sheath (not shown) of synthetic material may be used to get access to the venous system. Having reached the venous system, a long guiding metal wire (not shown) is advanced through the introduction sheath and via the venous system to the coronary sinus 24. This guiding wire and/or a delivery catheter is provided with X-ray distance markers so that the position of the device in the coronary sinus 24 may be monitored.

The elongate device in FIG. 21 (or the one in FIG. 21a) is locked onto a stent insertion device (not shown) so that the self-expandable stents 22 and 23 (or 22a and 23a) are held in a crimped, non-expanded state. Thereafter, the stent insertion device with the elongate device locked thereon is pushed through the introduction sheath and the venous system to the coronary sinus 24 riding on the guiding wire. After having obtained an exact positioning of the elongate device in the coronary sinus 24, as illustrated in FIG. 23 where the mitral valve annulus 25 and the mitral valve 26 having a central gap 27 are shown, the stent insertion device is removed. This will release the self-expandable stents 22 and 23 (or 22a and 23a) so that they expand and contact the inner wall of the coronary sinus 24 and thereby provide for a temporary fixation of the elongate device in the coronary sinus 24. Then, the guiding wire and the introduction sheath are removed.

Figure 24:
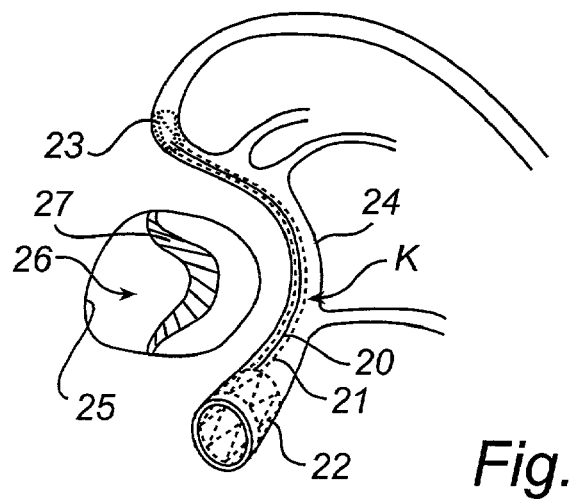
Figure 25:
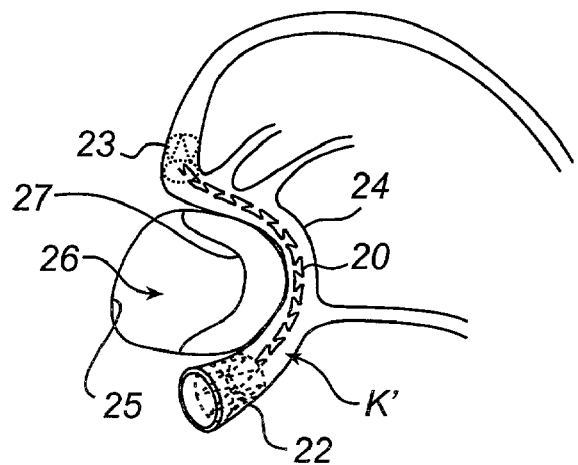

After the insertion, the self-expandable stents 22 and 23 (or 22a and 23a) will grow into the wall of the coronary sinus 24 while at the same time the resorbable sheath 21 (or restraining threads 21a) will be resorbed by the surrounding blood and tissue in the coronary sinus 24, as schematically illustrated in FIG. 24. When the resorbable sheath 21 (or resorbable threads 21a) has been resorbed to such a degree that it cannot hold the shape memory metal thread 20 (or the scissors-shaped member 20a) in its straightened state of shape any longer, the self-expandable stents 22 and 23 (or 22a and 23a) will be properly fixed into the wall of the coronary sinus 24 as a result of the normal healing process which always occurs after positioning a stent in a blood vessel. Then the shape memory metal thread 20 (or the scissors-shaped member 20a) retracts and the device is transformed to its activated shorter state of shape K', as illustrated in FIGS. 22 and 25 (corresponding to FIG. 22a). This shortening of the device makes it bend towards the mitral valve annulus 25, moving the posterior part thereof forward. This movement reduces the circumference of the mitral valve annulus 25 and thereby closes the central gap 27.

The device may be positioned by catheter technique or by any other adequate technique. It may be heparin-coated so as to avoid thrombosis in the coronary sinus 24, thus reducing the need for aspirin, ticlopedine or anticoagulant therapy. At least parts of the device may contain or be covered with drugs like Tacrolimus, Rappamycin or Taxiferol to be delivered into the tissue to prohibit excessive reaction from surrounding tissue. At least parts of the device may be covered with or contain VEGF (Vascular Endothelial Growth Factor) to ensure smooth coverage with endothelial cells.

Figure 26:
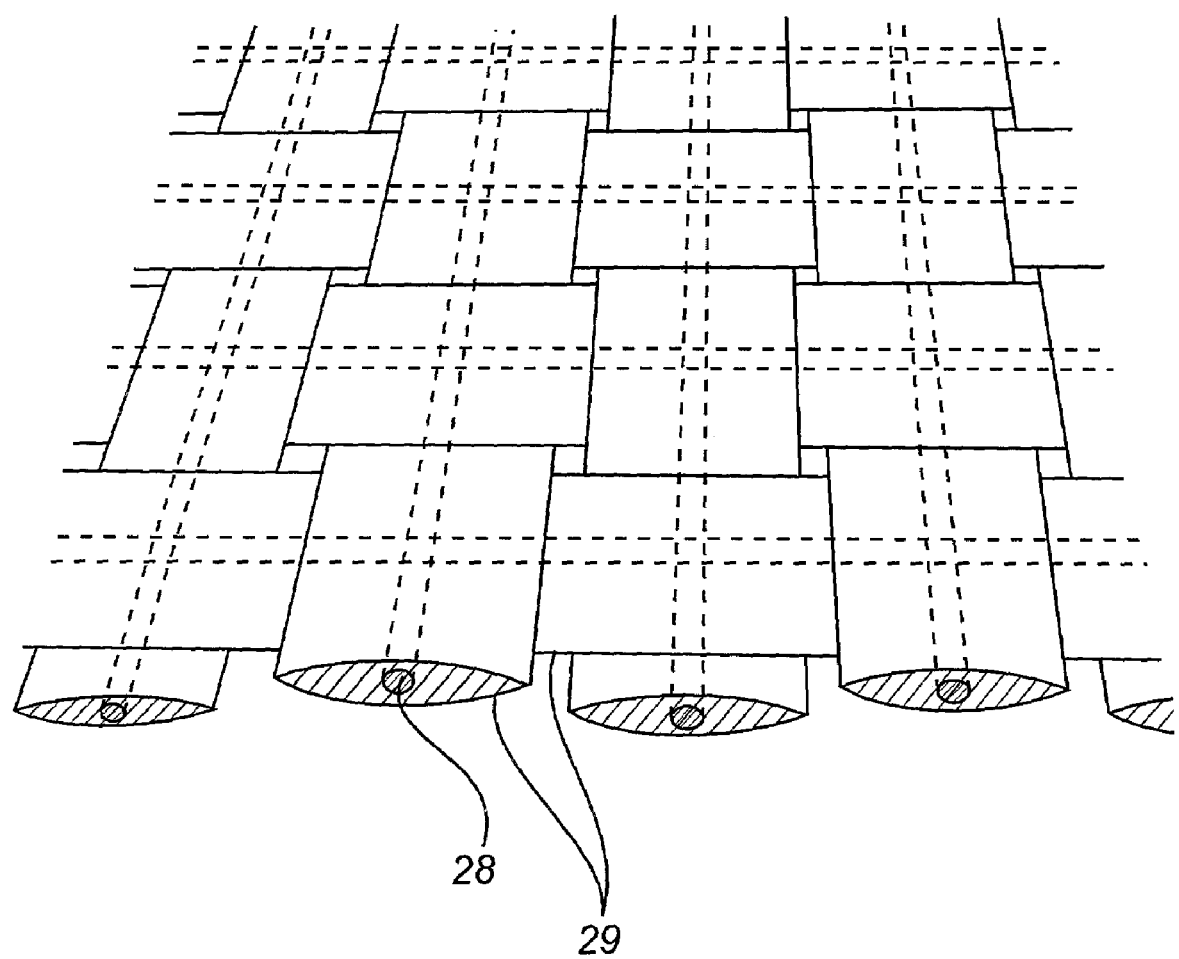
FIG. 26 is a schematic perspective view illustrating a part of one possible arrangement of a device according to the invention presenting a reshapable area.

FIG. 26 shows one possible arrangement of a part of a contractable area according to the invention. The contractable area comprises a shape-changing member in the form of a grid matrix of shape memory metal threads 28 covered by a delay means in the form of a fabric of a resorbable material (it should be noted that FIG. 26 was previously used to illustrate how the threads of the patches of FIGS. 19 and 20 may be covered with biocompatible material). The fabric comprises resorbable bands 29 which have been weaved together to form an area. Each of the resorbable bands 29 is solid except for a cylindrical hollow space in which a thread 28 is located, just like the thread 1 is located inside the tube 2 in FIG. 3.

The bands 29 restrain the threads 28 from being folded to their original curved shapes as long as the fabric 29 is not resorbed.

Analogously to the device in FIG. 3, there may be a radial play between the inner wall of each band 29 and the thread 28 being located inside it, in which play the thread 28 can move without consequently being able to change the size of the area of the device to any larger extent.

Further, the hollow space in each band 29 must not necessarily be cylindrical. In fact, if the width of each band 29 is small enough as compared to the curves that the threads 28 will assume when being "activated" as a result of the bands 29 being resorbed, the bands 29 may be hollow.

The contractable area in FIG. 26 may be manufactured by threading a thread 28 of a memory material into each resorbable band 29 and then weaving the bands 29 with threads 28 together to form the fabric as illustrated in FIG. 26.

Another possible way of making a contractable area according to the invention would be to arrange threads or bands of a memory material in a grid matrix and to fix the threads or bands together with resorbable crosslinks. The resorbable crosslinks would then restrain the threads or bands from being folded as long as enough resorbable material in the crosslinks is left unresorbed.

A contractable area according to the invention, as the one previously mentioned or as the one shown in FIG. 26, may be formed into a contractable sac as shown in FIGS. 27 to 30, which sac may be used to support a body organ or to restrain a pathologically growing body organ.

FIGS. 27 to 30 illustrate the use of a contractable sac 30 for treatment of pathological heart growth, according to another embodiment of the invention.

Figure 27:
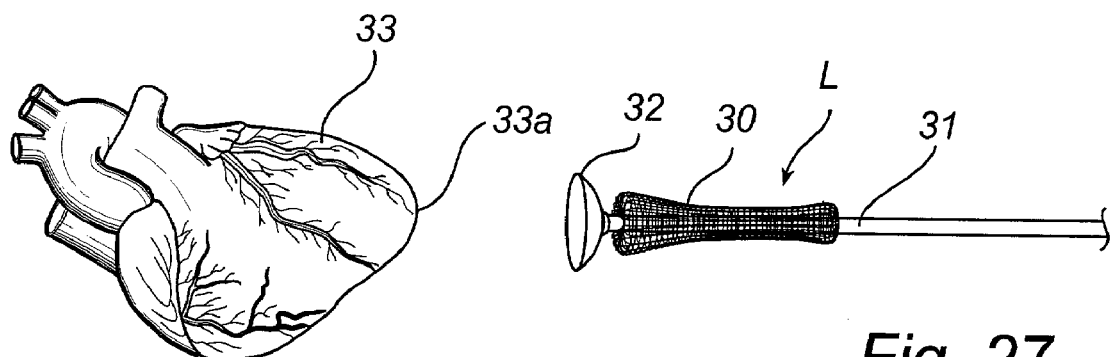
FIGS. 27–30 are schematic views illustrating the positioning and the contraction of an embodiment of the device according to the invention for treatment of pathological heart growth.

Referring to FIG. 27, the sac 30 in its non-activated state of shape L is threaded inside out on a catheter 31 with an anchoring means 32, here in the form of a suction cup 32, and the catheter 31 with the sac 30 is introduced to the apex cordis 33a of the heart 33 in known manner.

Figure 28:
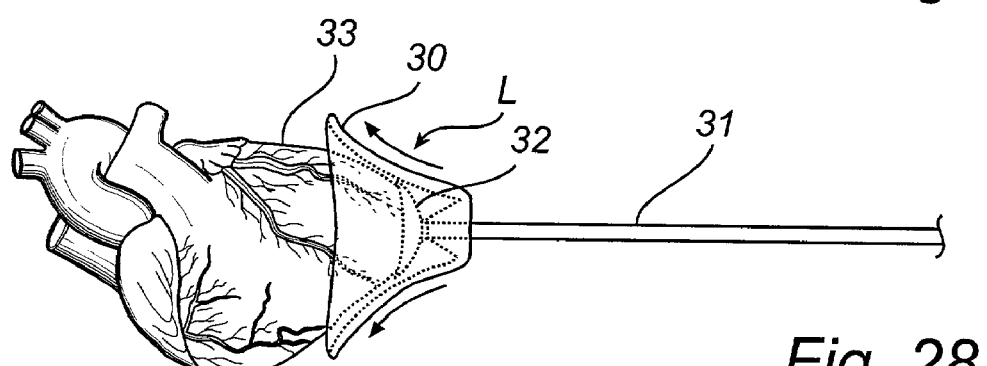

Now referring to FIG. 28, the suction cup 32 is put on the apex cordis 33a and the sac 30 is pushed off the catheter 31, by means of a catheter instrument (not shown), over the suction cup 32 and up over the heart 33.

Figure 29:
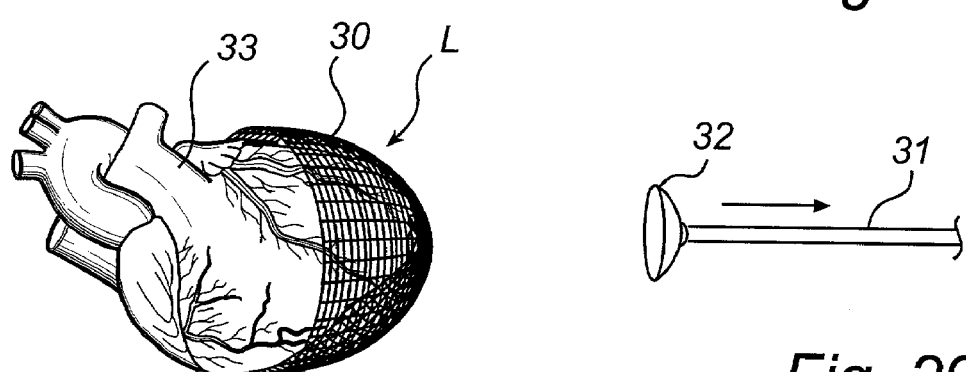

Now referring to FIG. 29, when the sac 30 is positioned round the heart 33, the suction cup 32 is pulled out through the bottom of the sac 30 and the catheter 31 is removed from the body.

Figure 30:
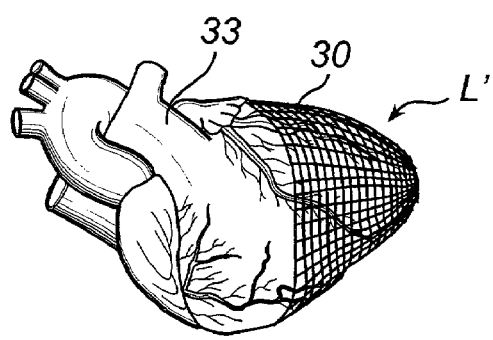

After a period of time, the resorbable material of the sac 30 will be resorbed and a restraining force by the shape memory metal threads against the heart 33 is released, and hence, the sac 30 is transformed to its activated state of shape L', as illustrated in FIG. 30. The sac 30 will then press itself tight round the heart 33 and apply a continuous restraining force on the heart 33, thus decreasing the heart size, or at least preventing the heart 33 from growing further.

A contractable area according to the invention can also be used as a contractable sheet for treatment of alveolar sac growth, e.g. in emphysematic pulmonary diseases.

Figure 31:
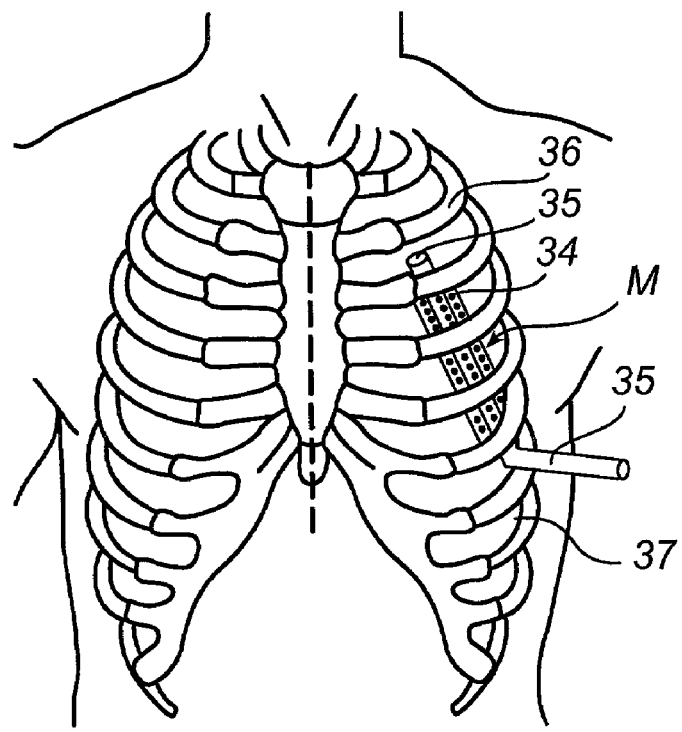
FIGS. 31 and 32 are schematic views illustrating the positioning of an embodiment of the device according to the invention for treatment of chronic obstructive pulmonary disease.
Figure 32:
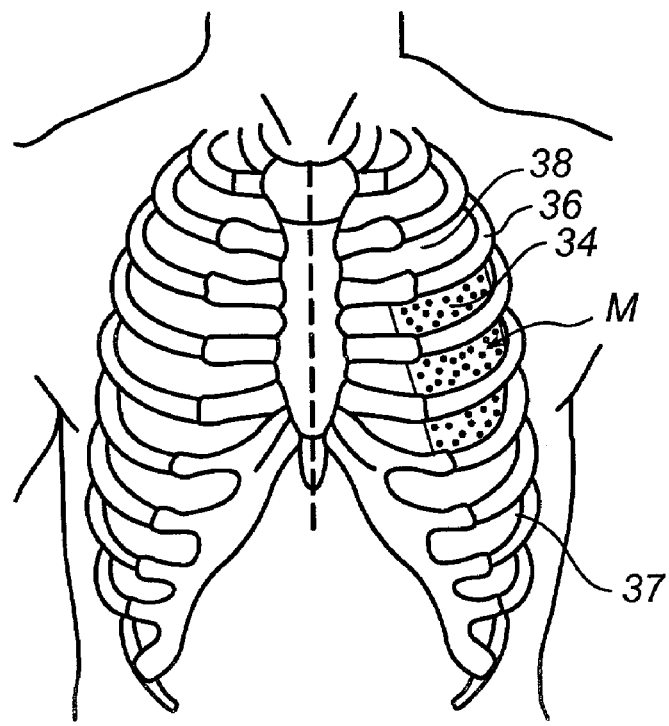

FIGS. 31 and 32 show the use of an embodiment of a device according to the invention for treatment of alveolar sac growth.

Referring to FIG. 31 a contractable sheet 34 in its non-activated state of shape M is rolled up on a catheter 35, introduced between ribs 36 into the pleural cavity (the space between the pleura of the lung and the pleura of the chest wall), and placed upon the lung 38 surface to be treated.

The contractable sheet 34 may also be inserted into the body by means of open surgery or by means of endoscopic surgery and positioned on an organ surface.

Now referring to FIG. 32, the sheet 34 is then rolled out over the lung 38 and the catheter 35 is removed.

The sheet 34 is arranged to grow fixed to the lung surface so that subsequent contraction of the sheet 34, as a result of the resorbable material of the sheet 34 being resorbed, causes the sheet 34 to compress the lung 38 by means of a force of the shape memory metal threads in the sheet 34. Hence, bullae and areas of enlarged alveolar sacs may be shrunk or eliminated and further pathological growth of alveolar sacs may be prevented.

In this embodiment the contractable sheet 34 contracts in two directions, one approximately vertical and one approximately horizontal. The sheet 34 could also be designed to contract in one direction only, e.g. the most horizontal one, or contract in a circular mode, and still be able to shrink bullous areas and prevent alveolar sacs from growing.

It is to be understood that modifications of the above described devices and methods can be made by people skilled in the art without departing from the spirit and scope of the invention.

The invention claimed is:

1. A medical device for reshaping a mitral valve annulus in a body, comprising:
   a shape-changing member having proximal and distal ends and biased to move from a first stretched configuration to a second configuration that is bent and shortened;
   a proximal self-expandable stent attached to the proximal end of the shape-changing member along a circumferential portion of the proximal stent and a distal self-expandable stent attached to the distal end of the shape-changing member along a circumferential portion of the distal stent, the proximal and distal self-expandable stents configured for anchoring the proximal and distal ends of the shape-changing member within a coronary sinus; and a resorbable material disposed along the shape-changing member, the resorbable material configured to maintain the shape-changing member in the first stretched configuration;

wherein, in the second configuration, the shape-changing member is configured to apply sufficient force to the coronary sinus to reshape the mitral valve annulus;

wherein the resorbable material has a design parameter to delay the bending and shortening to the second configuration until after expanded portions of the proximal and distal stents have sufficiently grown into an inner wall of the coronary sinus to support the bending and shortening to the second configuration.

2. The medical device of claim 1, wherein the shape-changing member is made of an elastic material.

3. The medical device of claim 1, wherein the shape-changing member is made of a material having superelastic properties.

4. The medical device of claim 1, wherein the shape-changing member is made of a shape memory material.

5. The medical device of claim 1, wherein the shape-changing member is made of a shape memory metal.

6. The medical device of claim 5, wherein the shape memory metal is Nitinol.

7. The medical device of claim 1, wherein the shape-changing member is made of a shape memory polymer.

8. A medical device for reshaping a mitral valve annulus in a body, comprising:

a shape-changing member made of a shape memory material, the shape-changing member having proximal and distal ends and biased to move from a first configuration to a bent second configuration having a different shape than the first configuration;

a proximal anchor fixed to the proximal end of the shape-changing member and a distal anchor fixed to the distal end of the shape-changing member, the proximal and distal anchors being expandable to engage an inner wall of a coronary sinus at a location adjacent the mitral valve annulus and at an opposed location on a posterior side of the inner wall of the coronary sinus; and a resorbable material disposed along the shape-changing member, the resorbable material configured to maintain the shape-changing member in the first stretched configuration;

wherein, in the second configuration, the shape-changing member is configured to apply sufficient force to the coronary sinus to reshape the mitral valve annulus;

wherein the resorbable material has a design parameter to delay the bending of the shape-changing member to the second configuration until after the proximal and distal anchors have been expanded to engage the inner wall of the coronary sinus and have sufficiently grown into the inner wall of the coronary sinus to support the bending to the second configuration; and wherein the shape-changing member comprises a scissor-shaped member having shaped memory material and the resorbable material is a thread located inside openings of the scissor-shaped member.

9. The medical device of claim 8, wherein the proximal and distal anchors each comprises a self-expandable cylindrical stent.

10. The medical device of claim 8 wherein the proximal anchor comprises:

a proximal stent fixed to the proximal end of the shape-changing member and the distal anchor comprises a distal stent fixed to the distal end of the shape-changing member.

11. The medical device of claim 8, wherein at least a portion of the device contains a vascular endothelial growth factor.

12. The medical device of claim 8, wherein the resorbable material comprises a thread disposed along the shape-changing member.

13. The medical device of claim 8, wherein the resorbable material comprises a sheath dispose over the shape-changing member, the sheath being located between the proximal and distal anchors such that the anchors may expand before the sheath is resorbed.

14. A medical device for reshaping a mitral valve annulus in a body, comprising:

a shape-changing member having proximal and distal ends and biased to move from a first configuration to a second configuration having a different shape than the first configuration;

a proximal anchor attached to the proximal end of the shape-changing member and a distal anchor attached to the distal end of the shape-changing member, the proximal and distal anchors being expandable to engage an inner wall of a coronary sinus at a location adjacent the mitral valve annulus and at an opposed location on a posterior side of the inner wall of the coronary sinus; and resorbable material engaging the shape-changing member to maintain the shape-changing member in the first configuration;

wherein the resorbable material has a design parameter to delay movement to the second configuration until expanded portions of the proximal and distal anchors have sufficiently grown into the coronary sinus to support the movement to the second configuration;

wherein, in the second configuration, the shape-changing member is configured to apply sufficient force to the coronary sinus to reshape the mitral valve annulus.

15. The medical device of claim 14, wherein the distal anchor is collapsed in a first configuration that is suitable for delivery into the coronary sinus and is expanded in a second configuration that is suitable to engage the coronary sinus when deployed.

16. The medical device of claim 15, wherein the distal anchor is a stent.

17. The medical device of claim 14, wherein the shape-changing member is elongated in the first configuration and shortened in the second configuration.

18. The medical device of claim 14, wherein the design parameter comprises a thickness of the resorbable material.

* * * * *